United States Patent
Ehrenpreis

(10) Patent No.: US 7,250,445 B1
(45) Date of Patent: Jul. 31, 2007

(54) ANTI-OXIDANT SUPPOSITORY FOR TREATING RADIATION PROCTOPATHY AND OTHER ANORECTAL DISORDERS

(76) Inventor: Eli D. Ehrenpreis, 8918 N. Keeler, Skokie, IL (US) 60076

( * ) Notice: Subject to any disclaimer, the term of this patent is extended or adjusted under 35 U.S.C. 154(b) by 0 days.

(21) Appl. No.: 11/035,513

(22) Filed: Jan. 14, 2005

(51) Int. Cl.
*A61K 31/355* (2006.01)
*A61K 31/34* (2006.01)
*A61K 31/07* (2006.01)

(52) U.S. Cl. ............... 514/458; 514/474; 514/725; 514/906

(58) Field of Classification Search ............ None
See application file for complete search history.

(56) References Cited

U.S. PATENT DOCUMENTS

| | | | | |
|---|---|---|---|---|
| 4,383,986 A | * | 5/1983 | Dubash et al. ........... 424/443 |
| 5,108,754 A | * | 4/1992 | Wilburn ............ 424/422 |
| 5,645,826 A | * | 7/1997 | Posner ............ 424/78.02 |
| 5,869,059 A | * | 2/1999 | Garza ............ 424/725 |
| 6,020,333 A | * | 2/2000 | Berque ............ 514/251 |
| 6,627,231 B2 | * | 9/2003 | Soldati ............ 424/766 |
| 6,893,648 B2 | * | 5/2005 | Mermelstein et al. ..... 424/401 |
| 2002/0037855 A1 | * | 3/2002 | Stanislaus ............ 514/18 |
| 2005/0053560 A1 | * | 3/2005 | Petrini et al. ............ 424/59 |

OTHER PUBLICATIONS

Remington's Pharmaceutical Sciences, 16th edition, published 1980 by by Mack Publishing Co., pp. 954-956.*

* cited by examiner

*Primary Examiner*—Raymond J Henley, III
(74) *Attorney, Agent, or Firm*—Jonathan D Feuchtwang

(57) ABSTRACT

A method for treating anorectal disorders, comprising a step of providing a suppository containing between 1000 and 500,000 IU of an antioxidant selected from the group of Vitamin A, Vitamin C, Vitamin E; and a step of placing the suppository within the rectal cavity for a period of time required for dissolution of the suppository.

5 Claims, No Drawings

ANTI-OXIDANT SUPPOSITORY FOR TREATING RADIATION PROCTOPATHY AND OTHER ANORECTAL DISORDERS

FIELD OF THE INVENTION

The invention is directed to methods and compositions for treating anorectal disorders. More particularly, the invention relates to methods and compositions for treating chronic anorectal disorders using vitamin A in a suppository form.

BACKGROUND OF THE INVENTION

The primary functions of the rectum and anus are storage of feces and maintenance of bowel continence. The rectum is a capacitance organ. The wall of the rectum is highly elastic and distensible. This allows for storage of fecal material prior to the act of defecation. The anal canal is made up of mucosal lining cells that cover two muscular layers (the internal and external anal sphincters). These sphincters, particularly the external anal sphincter, function to hold back feces from exiting the rectum by remaining contracted until the appropriate time to defecate. A variety of inflammatory, ischemic infectious, traumatic and neoplastic disorders may affect the anorectal region. Symptoms of anorectal disease include anal or rectal pain, urgency to move the bowels, fecal incontinence, diarrhea, rectal bleeding, and difficulty with evacuation of the rectum.

Vitamin A has been demonstrated to accelerate wound healing following burn injury and surgeries in laboratory animals. The mechanism of this effect is not been fully elucidated, but increased crosslinking of collagen and myofibrils occur after vitamin A administration.

The present inventor recently described a dramatic case of the patient with AIDS and anal carcinoma with developed a large radiation-induced anal ulceration with marked debility. The patient required high dose opioid therapy for control of anal pain. After a twelve week course of orally administered vitamin A (in the form of retinol palmitate), the patient experienced complete wound healing and symptomatic relief that persisted for more than six months. Radiation proctopathy is a form of injury of the rectum from radiation therapy administered for pelvic cancers such as cancers of the prostate, uterus and ovary. The present inventor recently designed, conducted and published a randomized double-blinded trial comparing vitamin A in the form of retinol palmitate (10,000 IU by mouth for 90 days) to placebo in patients with radiation proctopathy. The present inventor has found that vitamin A significantly reduced rectal symptoms of radiation proctopathy, due perhaps to the wound healing effects of vitamin A. It is assumed that administration of vitamin A in a suppository form would have even greater efficacy for radiation proctopathy and other chronic conditions of the rectum, since the suppository allows for delivery of large concentrations of vitamin A directly at the affected area of the rectum and anus. The other form of vitamin A, (beta carotene), when applied topically, have the potential to enhance the effectiveness of retinol palmitate for treating radiation proctopathy and other anorectal disorders.

Suppositories are bodies of solid materials into which medications have been incorporated. These medications are then placed into body cavities. Medications are released at the site of placement, resulting in local effects of the medications.

Suppository forms of medications are available for placement in the anus and vagina for the treatment of anorectal and gynecologic disorders. The most common use of rectal suppositories is for the treatment of constipation. Rectal suppositories are also used as an alternative form of drug delivery in patients that cannot receive medications by mouth. Examples of these types of rectal suppositories include treatments for nausea and pain.

There are numerous anorectal diseases that may benefit from topically applied vitamin A and anti-oxidant agents. These conditions include (but are not limited to), inflammatory bowel disease (IBD) including ulcerative proctitis and Crohn's disease, anal fissures, internal hemorrhoids, radiation proctopathy, anal and rectal neoplasms, anal warts, anal dysplasia, solitary rectal ulcer syndrome, *pruritis ani* and anorectal ischemia. These conditions represent a variety of significant clinical problems for which limited treatment options are currently available.

Anorectal disorders are diagnosed by medical history, physical examination, endoscopic evaluation with flexible sigmoidoscopy or colonoscopy, anorectal ultrasound, CT scan and MRI of the pelvis. By far, the most commonly used and most important of these diagnostic modalities are the endoscopic evaluations.

Current treatment modalities for anorectal disorders depend on the condition treated. Except for treatments for IBD and anal fissures, most treatment modalities have not undergone rigorous scientific evaluation and are primarily empiric. A variety of oral medications are used for these conditions.

Topical treatments for IBD consist of the anti-inflammatory agent 5-aminosalicylic acid, as well as hydrocortisone, a steroid. Topical therapies for anal fissure consist of agents that relax the anal sphincter muscles including nitroglycerin and calcium channel blockers. Topical therapies for internal hemorrhoids include suppositories containing local anesthetics and/or hydrocortisone. Topical 5-ASA and sucralfate have been recommended for radiation proctopathy, but appear to be ineffective. Short chain fatty acid enemas have been used to treat radiation proctopathy but are not readily available and difficult to administer. Topical creams and local anaesthetics are used for *pruritis ani*, but no suppositories have been tried. No topical agents have been tested for solitary rectal ulcer syndrome, anorectal neoplasms or anorectal ischemia. Many patients with these conditions remain symptomatic despite treatment using the aforementioned medications.

Thus, there is a need to develop methods and compositions that may be used to treat chronic anorectal disorders. Ideally, identification of new agents that may also alter the pathophysiology of chronic anorectal disorders is suggested.

SUMMARY OF THE INVENTION

The present invention provides a method for treating anorectal disorders. The method includes a step of providing a suppository containing between 1000 and 500,000 IU of an antioxidant selected from the group of Vitamin A. Other antioxidants such as Vitamin C (25-500 mg), and Vitamin E (100-1000 IU) may be included. The method further includes a step of placing the suppository within the rectal cavity for a period of time required for dissolution of the suppository.

Also disclosed is an anal suppository for use in treating anorectal disorders. The suppository includes a soluble base; and an antioxidant selected from the group of Vitamin A, Vitamin C, Vitamin E and other antioxidants encapsulated within the soluble base.

According to a preferred embodiment, the antioxidant contained within the anal suppository of the antioxidant is Vitamin A provided at a dosage of between 1000 and 500,000 IU.

According to a further aspect of the invention, the anal suppository may further include a second antioxidant selected from the group of Vitamin C, and Vitamin E and others such as green tea, etc. According to yet another aspect of the invention, the anal suppository may further include an anti-inflammatory agent and/or an anaesthetic agent.

DETAILED DESCRIPTION OF THE INVENTION

A variety of chronic, painful and debilitating disorders may affect the anorectal region. Examples of these disorders include IBD (ulcerative proctitis and Crohn's disease). Ulcerative proctitis is a chronic idiopathic disorder characterized by inflammation (edema, ulceration and bleeding) of the lining of the rectum. In anorectal Crohn's disease, chronic inflammation extends throughout the wall of the rectum and anus, resulting in deep ulcerations, fissuring and abscess formation as well as the findings seen in ulcerative colitis.

Anal fissure, when chronic, is a longstanding ulcer of the anoderm or skin surrounding the anus. Internal hemorrhoids are enlarged veins inside the anal canal that may become inflamed, causing bleeding and anal pressure.

Radiation proctopathy, a consequence of prior radiation for pelvic cancers causes defecation disorders due to damage and stiffness of the rectal wall and bleeding from new blood vessels that form as a response to decreased local bloodflow.

Neoplasms are abnormal growths of the anorectal region and may cause pain, ulcerations and rectal bleeding. Anorectal cancer generally occurs in patients developing anal warts from a virus called Human Pappiloma Virus (HPV). Longstanding anorectal infection with HPV causes dysplasia which may degenerate into anal cancer.

Solitary rectal ulcer syndrome occurs from decreased blood flow to the rectum due to anal spasm and prolapsing of the rectal wall through the anal canal. Large ulcerations and rectal bleeding commonly are present in patients with solitary rectal ulcer syndrome.

*Pruritis ani* or anal itching occurs in part from abnormalities of the anal sphincter.

Anorectal ischemia results from diminished blood supply to the anus and rectum related to a variety of conditions affecting the vascular system.

The present invention provides an inexpensive, innovative method for treating these conditions in mammals, including humans. The technique of the present invention is a substitute or adjunct for conventional treatments for these disorders. The device of the present invention provides an alternative to the conventionally used therapies for these conditions when available, and provides a new opportunity for treatment when no current therapies are available.

Vitamin A, a fat soluble vitamin, is present in pigmented vegetables and animal tissues. It is an important factor in growth of the epithelium, bone and retina.

Vitamin A has been demonstrated to have a number of beneficial qualities and is used as medical therapy for a variety of conditions. Vitamin A has been shown to enhance the function of the immune system, accelerates the rate of wound healing and may be used as treatment for precancerous conditions.

Administration of vitamin A and other anti-oxidants in a suppository form has the following potential advantages: 1) Larger doses will be delivered directly to the diseased area, resulting in more potent, better therapy for the conditions. 2) The amount of the delivered substance will undergo much less or no absorption into the systemic circulation. For certain substances, particularly vitamin A, no toxic effects of the compound will be seen. Administration of the oral form of vitamin A can cause damage to the liver, particularly in patients with preexisting liver disease or when large doses are given.

In a preferred embodiment, vitamin A in the form of retinol palmitate (with or without other forms of vitamin A including beta carotene) is incorporated into a suppository for application into the rectum for the treatment of anorectal diseases. This treatment is administered in a suppository form for patients suffering from chronic anorectal disorders. These treatments may be administered on a daily basis, or possibly more frequently. In an alternate use of the invention, vitamin A suppositories may be administered to patients with anal warts to prevent the development of anal dysplasia and anal cancer. Additionally, vitamin A suppositories would be administered to patients with anal dysplasia to prevent the development of anal cancer.

Suppositories may be constructed from fatty (or oleaginous) bases and/or water soluble (or miscible) bases.

Fatty bases include theobroma oil (also known as cocoa butter) with or without spermacetic or beeswax to raise the suppository melting point. Additionally, fatty bases for the vitamin A suppositories may include synthetic triglycerides and hydrogenated vegetable oils. These may include palm, palm kernel or coconut oils. Name brands utilized for production of vitamin A suppositories may include Fattibase, Wecobee FS, M, R or S, Dehydag, Hydrokote, Suppocire and Witepsol.

Water soluble bases may include glycerated gelatin, with or without preservatives, and polyethylene glycol polymers.

Suppositories may be constructed by hand rolling, compression molding or fusion molding methods.

The term "vitamin A" refers to the variety of chemicals having the same properties in the living organism as retinol. This term also includes specific chemicals that include retinol and retinol esters, as well as retinoids and chemical analogues from the retinoid family.

The term "anorectal" refers to the anatomic body structures beginning in the rectal portion of the lower intestine and extending the anal canal and anal sphincter muscles.

By "suppository," the invention includes the production of a solid substance that is administered into the rectum that contains medication for anorectal delivery.

The term "anorectal disease" refers to the group of abnormal conditions occurring in humans or animals that produce characteristic gastrointestinal symptoms and are associated with appropriate findings on physical examination and endoscopy.

"Endoscopy" is a diagnostic tool utilized to examine the lining of the gastrointestinal tract. In this setting, endoscopy of the anus and rectum is performed using an anoscope, sigmoidoscope or colonoscope.

The term "proctitis" used in the invention refers to inflammation of the lining of the rectum.

"Proctopathy" is used to denote a disorder of the rectum causing alteration of rectal function, but not limited to disorders resulting from inflammation.

The term "dysplasia" refers to premalignant or precancerous changes occurring in a body tissue.

The term "neoplasia" refers to abnormal cell growth that may be benign or malignant.

The term "IU" refers to international units of measure.

The invention provides methods and compositions for the treatment of anorectal disorders. More specifically the present invention discloses a suppository base containing an anti-oxidant that is placed in the rectum of a patient for a specific time period that allows for the treatment of chronic anorectal diseases. The use of a suppository to deliver the anti-oxidant, facilitates a more direct delivery of anti-oxidant to the affected region(s) of the body, and mitigates the toxicity problem associated with absorption of high amounts of anti-oxidants.

According to one embodiment, the suppository contains between 1000 and 500,000 IU of vitamin A in the forms of retinol palmitate and/or beta carotene. The suppository may be constructed from a variety of bases as previously described.

The suppository containing vitamin A is placed to reside within the rectal cavity for the time period required dissolution. Since the suppositories are fully dissolvable, release of vitamin A from the suppository will be achieved after residence of the suppository in the rectum. The released vitamin A will occur in high concentrations at the site of delivery, thus enhancing the effectiveness of this therapy for anorectal disorders.

According to an alternative embodiment, the suppository may consist of other antioxidants including vitamin E and vitamin C and natural antioxidants such as fish oils, green tea, cranberry, etc. These may be used as distinct suppository preparations or as additional components of the vitamin A suppositories.

These uses and in any of the embodiments of the invention, a suppository form of these agents are used as a clinical treatment for chronic diseases of the anus and rectum.

Any form of vitamin A that is placed in a suppository form for the treatment of anorectal diseases is within the confines of the invention. Additionally, the incorporation of vitamin A in combination with other antioxidants into suppositories technique to treat anorectal diseases is embodied within this invention. Additionally, the incorporation of any antioxidant substances within the suppositories, utilizing this technique as a means of treating anorectal disorders is embodied in the invention. Finally, other agents, such as anti-inflammatories, anaesthetics, herbals or other vitamins may be included in the suppositories to enhance the efficacy of the vitamin A. Substances utilized to produce the suppositories include any fatty (or oleaginous) bases and/or water soluble (or miscible) bases.

In particularly preferred embodiments, the medication contained in the suppository is vitamin A. In the preferred embodiment, the suppository is composed of fatty (or oleaginous) bases and/or water soluble (or miscible) bases. However, other bases may be employed in the invention to allow for the passage of the medication into the rectum. More generally, any form of suppository base may be used to construct the devise. In addition, a variety of antioxidants may be incorporated into the suppository to allow direct application of these substances to the rectum and anus. Other aforementioned substances may also be included in the suppositories to enhance their efficacy in treating anorectal disorders. The contents of the suppository may also consist of a variety of antioxidants, either alone or in combination with vitamin A, depending on the goal of treatment.

Variable doses of vitamin A may be utilized, depending on the condition being treated. For example, the oral dose of vitamin A used for the treatment of radiation proctopathy is 8,000 to 10,000 IU twice a day. Both lower and higher doses than these would initially be employed in the construction of the devise. The optimal dosage to treat these conditions will be determined based on clinical studies.

However, following appropriate clinical evaluation of this treatment, either larger or smaller doses of vitamin A may ultimately be used for treating radiation proctopathy as well as other anorectal disorders. Dosing for vitamin A and other antioxidants in suppositories are anticipated to be less than oral doses for the treatment of anorectal diseases, since these agents will be directly applied to the affected areas. However, higher doses may also be studied and utilized based on further clinical trials.

The foregoing description of the invention is illustrative only, and is not intended to limit the scope of the invention to the precise terms set forth. Further, although the invention has been described in detail with reference to certain illustrative embodiments, variations and modifications exist within the scope and spirit of the invention as described and defined in the following claims.

The invention claimed is:

1. A method for treating anorectal disorders selected from the group (ulcerative proctitis, ulcerative colitis, Crohn's disease, anorectal ischemia, neoplasms, inflammatory bowel diseases, anal cancer, radiation proctitis or proctopathy, and solitary rectal ulcer), said method comprising:
  providing a suppository containing at least one antioxidant selected from the group of Vitamin A, Vitamin C and Vitamin E, where the dosage of Vitamin A and Vitamin E is between 1000 and 500,000 IU, and the dosage of Vitamin C is between 25 and 500 milligrams; and
  placing the suppository within the rectal cavity for a time period required for dissolution of the suppository.

2. The method of claim 1, wherein the antioxidant within the suppository is Vitamin A.

3. The method of claim 2, wherein the antioxidant within the suppository further includes a second antioxidant selected from the group of Vitamin C, and Vitamin E.

4. The method of claim 1, wherein the suppository further includes an anti-inflammatory agent.

5. The method of claim 1 wherein the suppository further includes an anesthetic agent.

* * * * *